United States Patent [19]

Umezawa et al.

[11] Patent Number: 4,512,976

[45] Date of Patent: Apr. 23, 1985

[54] ANTIBIOTIC STUBOMYCIN AND PROCESS FOR THE PRODUCTION THEREOF

[75] Inventors: Iwao Umezawa, Tokyo; Kanki Komiyama; Hideo Takeshima, both of Kanagawa, all of Japan

[73] Assignee: The Kitasato Institute, Tokyo, Japan

[21] Appl. No.: 305,895

[22] Filed: Sep. 25, 1981

[30] Foreign Application Priority Data

Oct. 15, 1980 [JP] Japan .................................. 55-143017

[51] Int. Cl.$^3$ .......................... A61K 35/74; C12P 1/06
[52] U.S. Cl. ...................................... 424/122; 435/169
[58] Field of Search ......................... 424/122; 435/169

[56] References Cited

U.S. PATENT DOCUMENTS 4,181,715  1/1980  Kondo et al. ........................ 424/122
4,230,692  10/1980  Sehgal et al. ........................ 424/122

*Primary Examiner*—Jerome D. Goldberg
*Attorney, Agent, or Firm*—Young & Thompson

[57] ABSTRACT

This invention relates to the antibiotic stubomycin and process for producing same by culturing streptomyces sp KG - 2245 FERM-P No. 5675

2 Claims, 2 Drawing Figures

ANTIBIOTIC STUBOMYCIN AND PROCESS FOR THE PRODUCTION THEREOF

The present invention relates to a new antibiotic stubomycin and with a process for the production thereof.

The inventors of the present invention have found that microorganism strain No. KG-2245, newly isolated from a soil sample, belonging to the genus Streptomyces, produces a new antibiotic stubomycin.

The taxonomical properties of the strain KG-2245 are as follows:

A. Morphological properties

The aerial mycelia of KG-2245 are mostly rectiflexibles with hooks. The spores are cylindrical and the surface is smooth with minor irregularities (neither smooth nor typically warty or spiny), and the sizes are $0.47-0.67 \times 1.2-1.6 \mu$.

B. Cultural characteristics on various media

Cultural characteristics are shown in Table 1 (observation at 27° C., 10-14 days cultivation).

TABLE 1

Cultural properties of strain No. KG-2245

| Medium | Growth | Aerial mycelium | Reverse | Soluble pigment |
|---|---|---|---|---|
| Sucrose-nitrate agar | Poor | Ashes (5fe) | Silver gray (3fe) | Bamboo (2fb) |
| Glucose-nitrate agar | Moderate | Pussywillow gray (5dc) | Dusty orange (4lc) | Pastel orange (4lc) |
| Glycerol-calcium malate agar | Moderate | Maple (4le) | Light coral rose (6ga) | — |
| Glucose-asparagine agar | Good | Marigold (3na) | Yellow maple (3ng) | Amber (3lc) |
| Glycerol-asparagine agar | Good | Colonial yellow (2ga) | Amber (3pe) | Maize (2hb) |
| Inorganic salts-starch agar | Very poor | — | Orchid tint (10ba) | — |
| Tyrosine agar | Good | Oatmeal (2ec) | Yellow maple (3ng) | Maize (2hb) |
| Yeast extract-malt extract agar | Moderate | Rose beige (4gc) | Tile red (5ne) | Peach pink (5ea) |
| Oat meal agar | Moderate | Natural (3dc) | Sand (2ec) | Light beige (3ec) |
| Peptone-yeast extract-iron agar | Moderate | Ivory (2db) | Maize (2hb) | ± |
| Glucose peptone agar | Moderate | Orchid tint (10ba) | Bamboo (2fb) | Melon yellow (3ga) |
| Nutrient agar | Moderate | Rose beige (4gc) | Orange (4la) | Pastel orange (4lc) |

C. Physiological properties
1. growth temperature: possible at 37° C., optimum growth at 27°-30° C.
2. liquefaction of gelatine: positive
3. hydrolysis of starch: positive
4. peptonization of milk: negative
5. melanin production on tyrosin agar: negative
6. nitrate reduction: positive
7. cellulolytic activity: probable D. Utilization of carbon source
utilization: D-glucose, i-inositol
negative: L-arabinose, sucrose, raffinose, D-mannitol, D-fructose, cellulose
doubtful: D-xylose, rhamnose E. Cell wall composition Analysis of cell walls was made by the method of Becker et al., (Appl. Microbiol., 13, 236-243, 1965) and LL-diaminopimeric acid was found.

The various taxonomic properties hereinabove set forth clearly show the strain KG-2245 to be a microorganism belonging to the genus Streptomyces, and this microorganism was named Streptomyces sp. 2245. The strain was deposited in the Institute for Microbial Industry and Technology, Agency of Industrial Science and Technology, M.I.T.I., Japan, and assigned permanent deposit number FERM-P No. 5675.

This antibiotic stubomycin possesses antitumor activity and has the following physico-chemical properties:
1. Molecular formula: $C_{29}H_{35}NO_5$

| elemental analysis: | C% | H% | N% |
|---|---|---|---|
| found: | 72.33 | 7.35 | 2.83 |
| calculated: (as $C_{29}H_{35}NO_5$) | 72.58 | 7.47 | 2.80 |

2. Molecular weight: 477 (by mass spectrometery).
3. Melting point: 243°-245° C. (decomposed).
4. Optical rotation: +246 (C=0.5, dimethyl sulfoxide).
5. Ultraviolet absorption spectrum: as shown in FIG. 1; absorption peak at 300 nm ($\epsilon=44500$) in MeOH. The absorption peak did not shift under acidic or alkaline conditions.
6. Infrared absorption spectrum: as shown in FIG. 2; absorption peaks at 3470, 3260, 3040, 2925, 2870, 1640, 1605, 1540, 1455, 1440, 1385, 1350, 1330, 1260, 1220, 1195, 1160, 1120, 1090, 1005, 975, 930, 890, 835, 750, 700 $cm^{-1}$ in KBr.
7. Solubility: soluble in dimethyl sulfoxide, dimethylformamide pyridine slightly soluble in methanol insoluble in ethanol, benzene, acetone, chloroform, ethylacetate, water.
8. Color reaction: Positive: Rydon-Smith, Dragendorff, ferric chloride, and 2,4-dinitrophenylhydrazine reactions. Negative: ninhydrin, Ehrlich, and anisaldehyde-$H_2SO_4$ reactions.
9. Nature: lipophylic acidic substance.
10. Crystal form: colorless plates (from methanol).
11. Stability: stable under neutral and acidic conditions slightly unstable under alkaline conditions.
12. Thin-layer chromatography: $R_f=0.5$ (silica gel 60 F-254, Merck, solvent; $CHCl_3$—MeOH—AcOH, 91.5:7:1.5).

Stubomycin was compared with known antibiotics that have ultraviolet absorptions around 300 nm. Several antibiotics such as variotion [J. Antibiotics, 12A, 109 (1959)], ikarugamycin [J. Antibiotics, 25, 271 (1972)], viridenomycin [J. Antibiotics, 28, (3), 167 (1975)], and asukamycin [J. Antibiotics, 29 (9), 876 (1976)] were examined.

However, the molecular formula of variotion is $C_{17}H_{25}NO_3$, and the melting point and molecular weight of variotion differ from those of stubomycin. The melting points and molecular weights of ikarugamycin (253° C., 478), viridenomycin (169° C., 566), and asukamycin (188° C., 542) also differ from those of stubomycin.

Therefore, stubomycin is evidently a new antibiotic.

Figure 1:
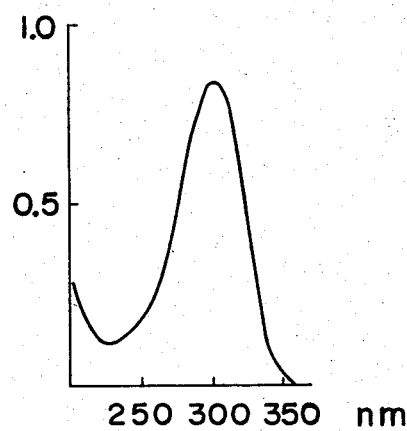
FIG. 1 is the ultraviolet absorption spectrum of stubomycin (MeOH)

Stubomycin is produced by culturing a microorganism belonging to the genus Streptomyces which produces antibiotic stubomycin and isolating it from the cultured broth.

According to the present invention, there can be used not only Streptomyces KG-2245 but also the natural or artificial mutants thereof, obtained by ultraviolet or X-ray radiation or by means of chemical mutagens, as well as other microorganisms belonging to the genus Streptomyces having stubomycin-producing activity, for the production of stubomycin.

In practicing this invention, Streptomyces sp No. KG-2245 which produces stubomycin is cultured in conventional media usually employed for antibiotics production. The cultivation can preferably be performed in a liquid medium; however, submerged aeration culture is advantageous for industrial production.

Among the conventional culture media, assimilable carbon sources such as glucose, sucrose, maltose, lactose, starch and molasses can be used. For the nitrogen source, organic nitrogen sources such as corn steep liquor, soybean meal, cotton meal, wheat glutens, peptone, meat extract, yeast extract, casein hydrolyzates, ammonium salts, nitrate salts and others can be used.

If desired, inorganic salts such as phosphates, magnesium salts, calcium salts, sodium salts, salt of copper, zinc, iron, manganese and others can be used. The pH of the culture medium is usually 6.8–7.0.

The temperature for culturation can be selected so as to predetermine the growth rate of the microorganism that produces stubomycin and is preferably 27°–30° C.

Although the fermentation period depends on the culture conditions, it can be terminated when maximum production of stubomycin has transpired in the medium, and is usually 2–7 days.

When isolating and purifying the stubomycin from the thus-cultured medium described hereinabove, and since stubomycin is in the form of a solution in the cultured filtrate or its supernatant, or is in the form of insolubles in the mycelia, it is advantageous to utilize the characteristics of stubomycin, for example its lipophilic acidic nature, its solubility in various solvents, or its ability to be absorbed on a carrier such as Sephadex LH-20, Dia-ion HP-20 or silica gel.

Stubomycin can be assayed by conventional microbioassay methods, using Bacillus subtilis as the test organism, ultraviolet absorption at 300 nm, and the color reaction of 2,4-dinitrophenylhydrazine.

An example of the isolation and purification of stubomycin is as follows:

The whole broth is filtered in a drum filter or a press filter, or cultured cells are removed in a basket-type centrifuge. Stubomycin can be recovered from the resulting broth filtrate by extraction with a variety of lipophilic water-immiscible and stubomycin-extracting solvents such as ethyl acetate, chloroform or methylene chloride under acidic conditions.

Stubomycin can also be isolated from mycelial cake with hydrophilic and stubomycin-extracting solvent such as methanol or acetone, under acidic conditions. These extracts are concentrated in vacuo, and the resultant residue is dissolved in methanol. This methanol solution is passed through a Sephadex LH-20 column, and the active fraction is adsorbed on a sulfuric-acid-treated silica gel column which is developed with methylene chloride to obtain purified stubomycin.

Sodium stubomycin can be isolated by adding an excess amount of sodium methoxide, sodium acetate or sodium 2-ethylhexanoate to the stubomycin-dissolving organic solvent such as methanol.

Sodium stubomycin is easily converted to stubomycin by treatment with a dilute solution of hydrochloric acid or sulfuric acid.

After sodium stubomycin is isolated from crude material including stubomycin by the method described above, then purified stubomycin can be obtained from sodium stubomycin by treatment with an acidic solution.

Potassium, calcium or aluminum stubomycin can also be obtained as pharmacologically acceptable stubomycin salts. The biological properties of stubomycin are as follows:

(1) Antimicrobial activity:

Minimum inhibitory concentration (MIC, $\mu$g/ml) against various microorganisms by the agar dilution method is shown in Table 2.

TABLE 2

Antimicrobial activity of stubomycin

| Test organism | MIC ($\mu$g/ml) | Test organism | MIC ($\mu$g/ml) |
|---|---|---|---|
| Bacillus subtilis PCI 219 | 0.4 | Candida albicans | >100 |
| Staphylococcus aureus FDA-209P | 3.1 | Saccharomyces sake | >200 |
| Mycobacterium smegmatis | 3.1 | Aspergillus niger | >100 |
| Sarcina lutea ATCC 1001 | 0.4 | Trichophyton interdigitalis | 6.3 |
| Escherichia coli NIHJ | >200 | Piricularia oryzae | 3.1 |
| Pseudomonas aeruginosa | >200 | Alternaria kikuchiana | 6.3 |
| Xanthomonas oryzae | >100 | Microsporum gypseum | 12.5 |

(2) Acute toxicity:

Acute toxicity ($LD_{50}$) in mice; approximately 400 mg/kg (i.p.), and over 1000 mg/kg (p.o.)

(3) Antitumor activity:

(A) Method

1. Male CDF mice were inoculated intraperitoneally (i.p.) with $1 \times 10^5$ cells of leukemia P388; and 24 hours after tumor inoculation, the mice were given stubomycin i.p. once a day for 9 days.

2. Male DDY mice inoculated i.p. with $2.5 \times 10^6$ cells of Ehrlich ascites carcinoma; and 24 hours after the inoculation, the treatment was started with the same schedule described above.

(B) Evaluation

The therapeutic efficacy of stubomycin on both tumors was calculated by observing the survival days of the mice and is given by the following:

$$\frac{\text{median survival days of treated group } (T)}{\text{median survival days of control group } (C)} \times 100 = \text{survival ratio } (T/C \%)$$

The results of therapeutic efficacy on leukemia P388 and Ehrlich ascites carcinoma are shown in Table 3.

TABLE 3

Antitumor activities of stubomycin on Ehrlich ascites carcinoma and leukemia P388

| Treatment schedule | Dose (mg kg/day) | Total dose (mg/kg) | MSD Ehrlich | MSD P388 | ILS Ehrlich | ILS P388 |
|---|---|---|---|---|---|---|
| Untreated | — | — | 19 | 12 | — | — |
| Day 1 | 75 | 75 | 28(1)* | 17 | 47 | 42 |
|  | 150 | 150 | 51 | 17 | 168 | 42 |
|  | 300 | 300 | 21 | 17 | 11 | 42 |
| Days 1, 5, 9 | 25 | 75 | 33(1) | 16 | 74 | 33 |
|  | 50 | 150 | 16 | 15 | −16 | 25 |
| Days 1~9 | 8.8 | 75 | 21 | 15 | 11 | 25 |
|  | 16.7 | 150 | 50(1) | 11 | 163 | −8 |
|  | 33.3 | 300 | 33(1) | 9 | 74 | −25 |

MSD: Median survival day.
ILS: Increased life span, expressed as percent increase over the untreated control mice.
*Number of cured mice.

The following examples illustrate the preparation and isolation of stubomycin.

EXAMPLE 1

One hundred milliliters of medium (glucose 2.0%, soybean meal 1%, peptone 0.3%, NaCl 0.3%, $CaCO_3$ 0.3%, $Na_2SO_4$ 0.2%, $K_2HPO_4$ 0.1%, KCl 0.05%, $MgSO_4$ 0.05%, $FeSO_4$ 0.01% by weight, pH 6.9) were placed in a 500 ml Sakaguchi flask and sterilized at 121° C. for 30 minutes. Streptomyces sp KG-2245 grown on Kreinsky medium at 28° C. for 10 days was inoculated therein and reciprocatingly shake-cultured at 27° C. for 4 days. After 4 days of cultivation, the contents of the flask were transferred to a 200-liter fermenter containing 150 liters of the sterilized medium described above. The fermentation was continued for 54 hours at 28° C., and 200 r.p.m. of agitation with aeration (150 l/min.) One hundred thirty liters of the cultured seed were inoculated into a 2-kiloliter fermenter containing 1.5 kiloliters of sterilized medium (glucose 2%, soybean meal 1%, NaCl 0.3%, $CaCO_3$ 0.3%, dry yeast 0.3%, pH 6.5).

The fermentation was continued for 148 hours at 28° C., and the medium was agitated at 200 r.p.m. and aerated at 1500 l/min. After the fermentation, the whole broth was filtered, and 212 kg of wet mycelial cake and 1300 l of filtrate were obtained.

The mycelial cake was mixed with 1500 l. of methanol and acidified with dilute hydrochloric acid to pH 2.0. After one hour agitation, the mixture was filtered and the methanol extract was passed through a column of Dia-ion HP-20 (100 l., Mitsubishi Kasei Co., Ltd.) The colorless active fraction was concentrated in vacuo and the residual gummy material was treated with diisopropyl ether to obtain 171 g of crude powder. The broth filtrate (1300 l.) was acidified with diluted hydrochloric acid to pH 2.0 and mixed with 650 l. of butyl acetate which was stirred for 30 minutes. The separated organic phase was dehydrated and then concentrated in vacuo. The residual gummy material was treated with n-hexane to obtain 6.3 g of crude powder. The crude powder (150 g) obtained from the mycelium and broth filtrate was suspended in 1 l. of 0.05M EDTA solution, and the suspension was agitated for 1 hr. The insoluble material was suspended in 1 l. of water and stirred at pH 2, adjusting for pH with diluted hydrochloric acid for 30 minutes.

The insoluble material was collected on filter paper, washed with water, and dried to obtain 60 g of pale yellow powder. The resulting powder (1.5 g) dissolved in methanol (200 ml) was chromatographed on a Sephadex LH-20 column (1.7 l.), and developed with methanol. The active fraction was concentrated in vacuo to obtain crystals of stubomycin (760 mg), which was recrystallized from methanol (yield: 450 mg).

EXAMPLE 2

To the pale yellow powder (17 g) obtained in Example 1, dissolved in hot methanol (5 l.), was added 20 ml of 44.3% (W/v) of sodium 2-ethyl hexanoate in methyl isobutyl ketone, and the mixture was stirred for one hour at room temperature. The mixture was then filtered and the precipitate was washed with methanol and vacuum dried to give 1.2 g of crystals. The residual solution was concentrated to about half of that volume, and stirred for 3 hours at room temperature. The resulting precipitate was separated, washed with methanol and dried to give 10.4 g of crystals. These crystals were suspended in 200 ml of 1N HCl, and stirred for 30 min. at 55° C. The precipitate was collected on filter paper, washed with water, and dried to obtain a white powder. This powder was dissolved in 5 l. of hot methanol, and 5 ml (23 mM) of sodium methoxide was added thereto. This solution was concentrated to half of that volume, and filtered, washed with methanol and dried to obtain 7 g of sodium stubomycin.

Elemental analysis: Calculated for $C_{29}H_{34}NO_5 \cdot Na \cdot H_2O$.

|  | C % | H % | N % |
|---|---|---|---|
| Found: | 66.98 | 7.33 | 2.53 |
| Calculated: | 67.27 | 7.01 | 2.71 |

UV: $\lambda_{max}^{MeOH} = 300$ nm ($\epsilon_{1\ cm}^{1\%} = 900$)
IR: 1620, 1480, 1450 $cm^{-1}$

EXAMPLE 3

Sodium stubomycin (5.5 g) obtained in Example 2 was suspended in 100 ml of 1N HCl, and stirred for one hour at 50°–60° C. Insoluble material was collected on filter paper, washed with water and dried to obtain 4.78 g of white powder. After being recrystallized from hot methanol, 3.33 g stubomycin was obtained.

What is claimed is:

1. Stubomycin having the following physico-chemical properties:
   (a) molecular formula: $C_{29}H_{35}NO_5$

| elemental analysis: | C% | H% | N% |
|---|---|---|---|
| found: | 72.33 | 7.35 | 2.83 |
| calculated: (as $C_{29}H_{35}NO_5$) | 72.58 | 7.47 | 2.80 |

(b) molecular weight: 477 (by mass spectrometry)

Figure 2:
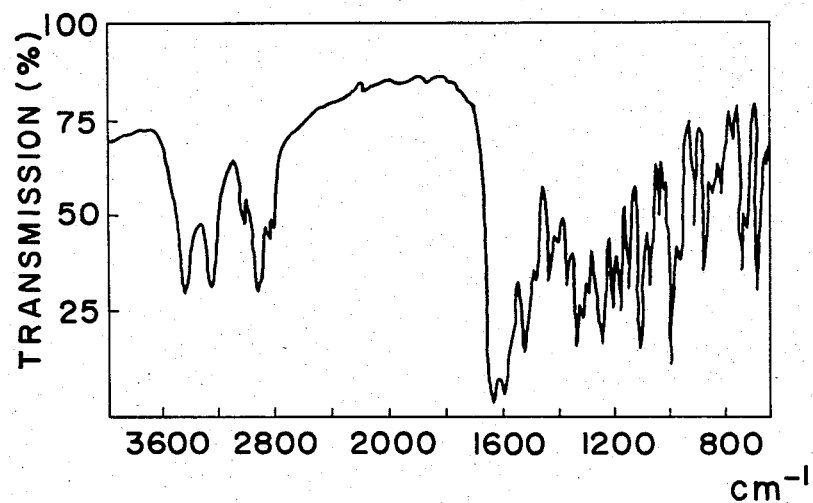
FIG. 2 is the infrared absorption spectrum of stubomycin (KBr).

(c) crystal form: colorless plates (from MeOH)
(d) melting point: 243°–245° C. (decomposed)
(e) optical rotation $[\alpha]_D^{20}$: +246° (C=0.5, dimethyl sulfoxide)
(f) ultraviolet absorption spectrum (in MeOH): as shown in FIG. 1
(g) infrared absorption spectrum (KBr): as shown in FIG. 2
(h) solubility:
   soluble: dimethyl sulfoxide, dimethylformamide, pyridine
   slightly soluble: methanol
   insoluble: ethanol, benzene, acetone, chloroform, ethylacetate, water
(i) color reaction:
   positive: Rydon-Smith, Dragendorff, ferric chloride, and 2-4-dinitrophenylhydrazine reactions
   negative: ninhydrin, Ehrlich, and anisaldehyde $H_2SO_4$ reactions
(j) nature: acidic substance
or its pharmaceutically acceptable salts.

2. A process for the production of stubomycin as defined in claim 1, which comprises culturing Streptomyces sp. KG-2245 FERM-P No. 5675 in a nutrient medium until substantial antibiotic activity is imparted to said medium, and isolating the thus-produced stubomycin from the cultured medium.

* * * * *